(12) United States Patent
Mahajan et al.

(10) Patent No.: US 8,883,730 B2
(45) Date of Patent: Nov. 11, 2014

(54) HUMAN LUNG SURFACTANT PROTEIN, SP-D, MODULATES EOSINOPHIL ACTIVATION AND SURVIVAL AND ENHANCES PHAGOCYTOSIS OF APOPTOTIC BOSINOPHILS

(75) Inventors: Lakshna Mahajan, Delhi (IN); Taruna Madan, Delhi (IN); Puranam Usha Sarma, Delhi (IN); Uday Kishore, Delhi (IN)

(73) Assignee: Council of Scientific and Industrial Research, New Delhi (IN)

( * ) Notice: Subject to any disclaimer, the term of this patent is extended or adjusted under 35 U.S.C. 154(b) by 992 days.

(21) Appl. No.: 11/906,117

(22) Filed: Sep. 28, 2007

(65) Prior Publication Data
US 2008/0255043 A1   Oct. 16, 2008

(30) Foreign Application Priority Data
Sep. 29, 2006   (IN) .......................... 2159/DEL/2006

(51) Int. Cl.
*A61K 38/00*   (2006.01)
*A61K 38/17*   (2006.01)
*C07K 14/785*   (2006.01)

(52) U.S. Cl.
CPC .................................. *A61K 38/395* (2013.01)
USPC ........ 514/15.5; 514/16.4; 514/18.2; 514/19.6

(58) Field of Classification Search
None
See application file for complete search history.

(56) References Cited

U.S. PATENT DOCUMENTS 6,838,428 B2    1/2005  Whitsett
2004/0259201 A1* 12/2004  Clark et al. ................ 435/69.1

FOREIGN PATENT DOCUMENTS

| WO | WO 00/23569   | * | 4/2000 |
| WO | WO03/035679   | * | 5/2003 |
| WO | WO2004/091436 | * | 10/2004 |
| WO | 2007/056195 A2 |   | 5/2007 |
| WO | WO2007/056195 | * | 5/2007 |

OTHER PUBLICATIONS

Gallin ('Quantitative and Qualitative Disorders of Phagocytes', In: Harrison's Principles of Internal Medicine, 13th Ed., Isselbacher et al, Ed.s, 1994, p. 336).*
Ribeiro et al (Journal of Clinical Pathology, 1993, vol. 47, pp. 672-673, see Figure 1).*
Whitsett, JA, 2005"Surfactant proteins in innate host defense of the lung," Biol Neonate 88(3); 175-80, Review.
Madan, T., et al. 1997 "Lung surfactant proteins a and D can inhibit specific Igl binding to the allergens of *Aspergillus fumigatus* and block allergen-induced histamine release from human basophilis", *Clin. Exp. Immunol.*, 110:241-249.

(Continued)

*Primary Examiner* — Karen Canella
(74) *Attorney, Agent, or Firm* — Ladas & Parry LLP

(57) ABSTRACT

The present invention provides the use of formulation with surfactant protein-D (SP-D) in the modulation of activity of human eosinophils derived from hypereosinophilic patients to an increased activation state and increased apoptosis. Accordingly the utility of the invention can be extended in human subjects in resolution of eosinophilic inflammations in related diseases and disorders like neuromuscular and respiratory diseases with eosinophilia other than airway-hyperresponsiveness, allergy and asthma, hypereosinophilic leukemias, hypereosinophilc syndromes (rare hematological diseases), skin diseases like eosinophilia-Myalgia syndrome, eosinophilic fascitis, capillary leak syndromes (IL-2), Churg-Strauss syndrome, toxic oil syndrome, parasitosis, etc., where a large number of stimulated eosinophils accumulate and release a series of growth factors, cytokines, chemokines, bioactive lipid mediators, toxic oxygen metabolites.

7 Claims, 4 Drawing Sheets

(56) References Cited

OTHER PUBLICATIONS

Figure 1:
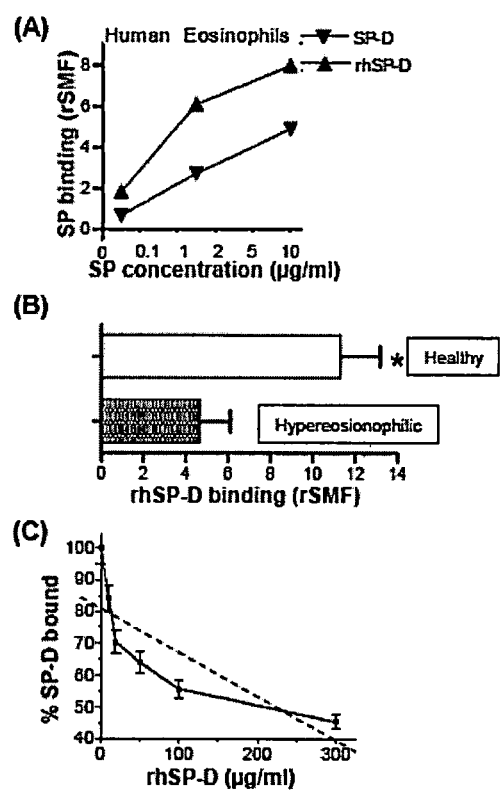

Palaniyar, N. et al. 2003, Surfactant protein D bind genomic DNA and apoptotic cells and enhances their clearance, in vivo, *Ann. N. Y. Acad. Sci.*, 1010:471.

Mahajan, et al. *Journal of Allergy and Clinical Immunology*, vol. 117, Issue 2, Supplement 1, Feb. 2006, p. S64 Abstract 251.

von Bredow C., et al. 2006, Surfactant protein D regulates chemotaxis and degranulation of human eosinophils, *Clin Exp Allergy*, 36(12:1566-1574).

Bunc M., et al. 2001, "The idiopathic hypereosinophilic syndrome", 2001, *Eur J. Emerg Med.* 8(4):325-30.

Strong, P., et al. 1998 "A novel method of purifying lung surfactant proteins A and D from the lung lavage of alveolar proteinosis patients and from pooled amniotic fluid" *J Immunol Methods*, 220, 139-49.

Hebestreit, H. et al. 1996 "Expression and function of the Fas receptor on human blood and tissue eosinophils" *Eur J Immunol* 26, 1775-80.

Rothenberg, M. E. 1998, "Eosinophilia", *The New England Journal of Medicine*, 338(22): 1592-1600.

Posada de la Paz M., Philen RM, Borda AI. 2001, Toxic oil syndrome: the perspective after 20 years, *Epidemiol Rev.*, 23(2):231-47, Review.

Crouch EC, "Surfactant protein-D and pulmonary host defense", *Respir Res.*, 1(2):93-108, Review.

Madan, T., Kaur, S., Saxena, S., Sigh, M., Kishore, U., Thiel, S./, Reid, K.B & Sarma, P.U. (2005a), "Role of collectins in innate immunity against aspergillosis", *Med Mycol* 43 Suppl 1, S155-63.

Wang, J. Y., Shieh, C.C., You, P.F., Lei, H.Y., and Reid, K.B.M., 1998, "Inhibitory effect of pulmonary surfactant proteins A and D on allergen induced lymphocyte proliferation and histamine release in children with asthma", *Am. J. Respir. Crit. Care Med.*, 158:510-518.

Borron, P.J., et al., 1998, "Recombinant rat surfactant-associated protein D inhibits human T lymphocyte proliferation and IL-2 production", *J. Immunol.* 161:4599-4603.

Singh, M., T. Madan, P., Waters, S.K., Parida, P.U. Sarma, and U. Kishore, 2003, Protective effects of a recombinant fragment of human surfactant protein D in a murine model of pulmonary hypersensitivity induced by dust mite allergens, Immunol., Lett, 86:299-307.

Madan, T., Kishore, U., Singh, M., Strong, P., Clark, H., Hussain, E.M., Reid, K.B., and Sarma, P.U., 2001, Surfactant proteins A and D protect mice against pulmonary hypersensitivity induced by *Aspergillus fumigatus* antigens and allergens, *J. Clin. Invest.*, 107:467.

Kishore U, Greenhough Li, Waters P, Shrive AK, Ghai R, Kamran MF, Bernal AL, Reid KB, Madan T, Chakraborty T., Surfactant proteins SP-A and SP-D: structure, function and receptors, *Mol Immunol.*, Mar. 2006:43(9): 1 293-315.

Kishore, U., Wang, J.Y., Hoppe, H. J., & Reid, K.B, 1996, "The alpha-helical neck region of human lung surfactant protein D is essential for the binding of the carbohydrate recognition domains to lipopolysaccharides and phospholipids", *Biochem J*, 318 (Pt 2), 505-11.

Koenderman, L., Kok, P.T., Hamelink, M.L., Verhoeven, A.J. & Bruijnzeel, P.L., 1988, "An improved method for the isolation of eosinophilic granulocytes from peripheral blood of normal individuals", *J Leukoc Biol* 44, 79-86.

Roufosse, Florence, Goldman, Michel and Cogan, Elie, "Idiopathic Hypereosinophilic Syndrome", *Orphanet*, Dec. 2004.

N. Segal, Y. Levy, B. Garry, Y.L. Danon; "Prevalence and Causes of Moderate-Severe Eosinophilia in Children", *J Allergy Clin Immunol*, Feb. 2006.

L. Mahajan, S.D. Telang, U. Kishore, V.K. Singh, C.N. Ramchand, P.U. Sarma, T. Madan, "Direct Interaction of Recombinant Human Surfactant Protein-D (rhSP-D) Modulates Human Eosinophil Activation, Their Rate of Apoptosis and Clearance by Macrophages", *J Allergy Clin Immunol*, Feb. 2006.

\* cited by examiner

HUMAN LUNG SURFACTANT PROTEIN, SP-D, MODULATES EOSINOPHIL ACTIVATION AND SURVIVAL AND ENHANCES PHAGOCYTOSIS OF APOPTOTIC BOSINOPHILS

FIELD OF THE INVENTION

The present invention generally relates to use of a formulation for induction of and/or increasing apoptosis in activated eosinophils using human lung surfactant protein D in eosinophil mediated diseases and disorders other than airway-hyperresponsiveness, allergy or asthma. Salient eosinophil-mediated disorders are eczema, eosinophilic cardiomyopathy, eosinophilic gastroenteritis, hypereosinophilic syndrome, graft versus host disease, chronic fibrosis, a parasitic inflammatory disorder, drug reaction, eosinophilic pneumonias, episodic angioedema with eosinophilia, inflammatory bowel disease, eosinophilic leukemia and/or food enteropathy and hypereosinophilia associated diseases that include infections, cirrhosis and cancer. Various diseases in which numbers of eosinophils greatly increase in the peripheral blood and/or tissues and result in the histotoxic conditions include neuromuscular diseases with eosinophilia, hypereosinophilic leukemias, hypereosinophilc syndromes (rare hematological diseases), skin diseases like eosinophilia-Myalgia syndrome, eosinophilic fascitis, capillary leak syndromes (IL-2), Churg-Strauss syndrome, toxic oil syndrome, parasitosis, respiratory diseases including chronic sinusitis, etc and few of these are described below (1, 2). The invention specifically relates to the use of formulation with human lung surfactant protein-D for increased apoptosis of human eosinophils derived from patients with peripheral eosinophilia. The invention also relates to the use of formulation with surfactant protein-D (SP-D) in patients for inducing increased apoptosis in activated and/or cytokine primed eosinophils (e.g. IL-5 primed eosinophils). Accordingly the utility of the invention can be extended in human subjects for use of formulation with complete or a fragment of native or recombinant human lung surfactant protein D for resolution of eosinophilia and tissue infiltrations in eosinophilic disorders.

BACKGROUND AND PRIOR ART

Lung surfactant protein D (SP-D) is involved in pulmonary surfactant homeostasis and is one of the collectins belonging to a family of oligomeric proteins consisting of a collagen region linked to a C-type lectin domain via an α-helical neck region. The structural subunits of SP-D are homotrimers of these chains, and the subunits are themselves oligomerized into cross-like tetramers and higher oligomers (3). SP-D binds to oligosaccharides on the surface of a variety of pathogenic microorganisms and induces aggregation. It initiates several effector mechanisms including the recruitment of inflammatory cells to destroy the pathogens. SP-D enhances the binding of influenza A virus to neutrophil granulocytes and promotes the neutrophil respiratory burst in response to the virus. It binds directly to alveolar macrophages in the absence of microbial ligands, and generates oxygen radicals (3, 4, 5). In addition to its role in antimicrobial defense, SP-D also seems to have an immunomodulatory function, inhibiting T lymphocyte proliferation and IL-2 production as well as inhibiting specific IgE binding to allergens and blocking allergen-induced histamine release from human basophils, incorporating the properties of modulating lung immune response in the lung allergic disease condition (6, 7, 8).

Owing to the above properties, SP-D was shown to offer protection in allergic murine models of pulmonary hypersensitivity to fungal (*Aspergillus fumigatus*) and Derp allergens with significant reduction in antigen-specific IgE levels, blood eosinophilia and pulmonary cellular infiltration (9, 10).

Erpenbeck (2006) also showed inhibition of allergen-induced early airway response, reduced airway hyperresponsiveness and reduced eosinophilia in bronchoalveolar lavage and lung tissues, on treatment with SP-D, also suggesting its role in modulating lung immune response in the pulmonary allergic disease condition (11). Palaniyar et al, showed that SP-D increases clearance of apoptotic pulmonary macrophages (12). Mahajan et al, 2006, showed that SP-D interacts with eosinophils and increased clearance of apoptotic eosinophils by macrophage cell line and they also showed that SP-D increases survival and decreases apoptosis in eosinophils from healthy human subjects (13). This observation is exactly opposite to the subject matter of this patent where SP-D decreases survival and increases/induces apoptosis in eosinophils from patients of hypereosinophilia and cytokine activated eosinophils. Activated eosinophils are secreting inflammatory cytokines and mediators and contribute to pathogenesis. Apoptotic eosinophils are eosinophils which are undergoing a programmed cell death. SP-D induces apoptosis in activated eosinophils only.

A recent study in December 2006 has appeared on SP-D interaction with human eosinophils in the journal, Clinical and Experimental Allergy. The study also showed direct interaction of SP-D with human eosinophils isolated from healthy normals through its CRD that resulted in inhibition of eotaxin triggered chemotaxis and ECP-degranulation stimulated by Ca2+ ionophore in the eosinophils (14). This study did not evaluate effect of SP-D on eosinophils from patients or activated eosinophils and did not evaluate apoptosis.

Novelty of the present invention is in inducing increased apoptosis in eosinophils from patients and activated eosinophils in presence of SP-D. Persistence of apoptotic eosinophils leads to increased tissue damage in eosinophilia hence their clearance is very essential. Eosinophil infiltration into the tissue is caused due to eosionphil activation caused by allergens or any other idiopathic mediator.

A few compounds have been shown to help in induction and clearance of apoptotic eosinophils, however, this is the first report of SP-D involvement in induction of apoptosis in eosinophils derived from patients and activated eosinophils.

SP-D has also been indicated to be useful for the prevention and diagnosis of pulmonary emphysema (U.S. Pat. No. 6,838, 428) (15). Emphysema is a type of chronic obstructive pulmonary disease (COPD) involving damage to the air sacs (alveoli) in the lungs. As a result, your body does not get the oxygen it needs. Emphysema makes it hard to catch breath along with a chronic cough and trouble in breathing during exercise.

Clark et al, have filed a patent on recombinant surfactant protein D compositions and methods of use thereof (United States Patent 20040259201) wherein they describe an rSPD (n/CRD) polypeptide, fragment, homologue, variant or derivative thereof for use in a method of treatment or prophylaxis of a disease wherein said disease or disorder comprises an inflammatory disease selected from the group consisting of allergy and inflammatory lung disease, allergy to the house dust mite (*Dermatophagoides* sp), a fungus or fungal spores of *Aspergillus fumigatus*, microbial infection of the lung. They also claim a method of reducing airway hyperresponsiveness, serum IgE levels or eosinophilia in an individual, the method comprising administering to the individual an rSPD(n/CRD) polypeptide and a method of reducing alveolar macrophage number in an individual, the method comprising administering to the individual an rSPD(n/CRD) polypeptide that enhances the clearance of apoptotic alveolar macrophages, or enhances the clearance of necrotic alveolar macrophages, or both (16). The patent specifically mentions use of SP-D for reducing eosinophilia associated with airway hyper-responsiveness and this is not in conflict with our proposed claims of use of a formulation comprising of SP-D for inducing apoptosis in eosinophils derived from patients and activated eosinophils and reducing eosinophilia in eosinophil mediated diseases other than airway hyper-responsiveness.

Machiko and Whitsett (Patent: WO2007056195) have patented SP-D for prevention and treatment of lung infections and sepsis. Surfactant protein D (SP-D) is a member of the collectin family of collagenous lectin domain-containing proteins that is expressed in epithelial cells of the lung. Administration of SP-D protein or fragments thereof is useful for the prevention or treatment of sepsis or lung infection (17).

The invention WO03035683 by Lyster et al, describes a novel form of surfactant protein D (SP-D). It discloses a specific in vitro SP-D assay and a method to detect an increased risk for the development of atherosclerosis (18).

The earlier studies from our group and others proposed the inhibitory effect of SP-D on T cell proliferation and thereby reduction in Th2 type of cytokines namely IL-4, IL-5 and IL-13 are probably responsible for downregulation of eosinophilia in mice treated with native or recombinant SP-D (19, 20). We for the first time show that direct interaction of SP-D with activated eosinophils (eosinophils secreting ECP, MBP and other molecules resulting in desquamation of epithelium and resulting in tissue damage observed in eosinophil mediated diseases) resulted in induction and increase of apoptosis in them.

Eosinophils are primarily thought of as hematopoietic cells. Whereas eosinophils normally account for only 1-3% of circulating leukocytes their numbers greatly increase in the peripheral blood and tissues in a variety of human diseases. Any perturbations that results in systemic or local eosinophilia can have profound effects on a patient. Salient eosinophil-mediated disorders are eczema, eosinophilic cardiomyopathy, eosinophilic gastroenteritis, hypereosinophilic syndrome, graft versus host disease, chronic fibrosis, a parasitic inflammatory disorder, drug reaction, eosinophilic pneumonias, episodic angioedema with eosinophilia, inflammatory bowel disease, eosinophilic leukemia and/or food enteropathy and hypereosinophilia associated diseases that include infections, cirrhosis and cancer. Various diseases in which their numbers greatly increase in the peripheral blood and/or tissues and result in the histotoxic conditions include neuromuscular diseases with eosinophilia, hypereosinophilic leukemias, hypereosinophilc syndromes (rare hematological diseases), skin diseases like eosinophilia-Myalgia syndrome, eosinophilic fasciitis, capillary leak syndromes (IL-2), Churg-Strauss syndrome, toxic oil syndrome, parasitosis, respiratory diseases including chronic sinusitis, etc and few of these are described below (1, 2).

Neuromuscular diseases with eosinophilia involve a number of disorders associated with variable degrees of muscle, peripheral nerve, and connective tissue involvement. These include diffuse fasciitis or Shulman syndrome, eosinophilic myositis and eosinophilic polymyositis (1, 2, 21).

The hypereosinophilic syndrome (HES) encompasses clinical manifestations sharing 3 features (1) a peripheral eosinophil count of greater than $1.5 \times 10^9$/L for longer than 6 months; (2) evidence of organ involvement (cardiac and neurologic systems), excluding benign eosinophilia; and (3) an absence of other causes of eosinophilia, such as parasite infestation (most common cause of eosinophilia worldwide), allergy (most common cause of eosinophilia in the United States), malignancy, and collagen vascular disease (22).

Eosinophils in HES infiltrate multiple organs where they inflict tissue damage through the release of granule proteins. They also release proinflammatory cytokines (ie, interleukin 1 alpha, tumor necrosis factor-alpha, interleukin 6, interleukin 8, IL-3, IL-5, GM-CSF, macrophage inflammatory protein), which attract more eosinophils and other inflammatory cells to the area. The HES presentation can be acute (eg, stroke), as when cardiac and neurologic systems are involved, or, more commonly, HES has an insidious onset. In an NIH series, common symptoms included fatigue (26%), cough (24%), breathlessness (16%), muscle pains or angioedema (14%), and fever (12%). Mucocutaneous manifestations occur in 25-50% of patients. Cardiac involvement is the most common cause of mortality in HES. Some cases of HES turn into leukemia, and, as such, chromosomal abnormalities are at the root of some cases of HES.

Eosinophilic cellulitis (Wells syndrome) is an uncommon condition of unknown etiology. The presentation usually involves a mildly pruritic or tender cellulites like eruption with typical histologic features characterized by edema, flame figures, and a marked infiltrate of eosinophils in the dermis.

Eosinophilia-myalgia syndrome (EMS) is a disorder that causes inflammation by eosinophils in nerve, muscle, and connective tissue, which may include the fascia (as in Eosinophilic fascitis). EMS is an illness characterized by pruritus, cutaneous lesions, edema, sclerodermoid changes, and joint pain, in addition to dramatic myalgia and eosinophilia. This phase lasts weeks to months and is followed by a chronic phase characterized by sclerodermoid skin changes, neuropathy, neurocognitive deficits, continued myalgia, and muscle cramps. Other less common chronic manifestations involve the pulmonary, cardiac, and gastrointestinal systems (23).

Molecular events leading to Eosinophilia: Three cytokines, granulocyte-macrophage colony-stimulating factor (GM-CSF), interleukin 3 (IL-3), and interleukin 5 (IL-5) have been shown to promote the growth and the maturation of eosinophils and to induce the conversion of normal eosinophils to hypodense eosinophils. In particular, IL-5 activity is shown to be elevated in sera from patients with EMS. Therefore, in EMS, IL-5 may play a substantial role in the growth and the stimulation of eosinophils and in their conversion to the hypodense, cytotoxic form. Hypodense eosinophils are activated cells with increased survival and an increased capacity for cytotoxicity, and release inflammatory mediators, such as leukotrienes, histo-toxic cellular components, growth factors, cytokines, chemokines, bioactive lipid mediators, toxic oxygen metabolites, etc to the exterior and cause damage. The delayed eosinophil apoptosis makes a significant contribution to the increased tissue load of eosinophils.

In view of the role of eosinophils in diseases, the present invention is aimed at providing the use of formulation with SP-D in resolution of eosinophilic inflammations by inducing and/or increasing apoptosis in activated eosinophils towards the beneficial effects.

The present invention generally relates to a novel interaction of Surfactant protein-D with human eosinophils, wherein the molecule, induced and increased apoptosis of activated eosinophils derived from peripheral blood of individuals with hypereosinophilia.

Further in the present study, purified native human SP-D (native) has been used. Also, a recombinant homotrimer containing eight gly-x-y collagen repeat sequences, an alpha-helical, coiled-coil neck region, and the carbohydrate recognition domain of SP-D, a functionally active molecule expressed as inclusion bodies in *Escherichia coli* was used (24).

OBJECTS OF THE INVENTION

The main object of the invention is to provide the use of a formulation for inducing and/or increasing apoptosis in activated eosinophils comprising of complete or fragment(s) of native or recombinant human lung surfactant protein D (SP-D). SP-D induces and increases apoptosis specifically in activated eosinophils derived from hypereosinophilic patients for the resolution of eosinophilia and eosinophil mediated pathogenic effects in eosinophil related diseases and disorders.

Another object of the invention is the differential modulation of activity and apoptosis in eosinophils derived from hypereosinophilic patients and healthy donors on direct interaction with lung surfactant protein-D (SP-D) formulation.

Another object of the invention is the differential modulation for increase in apoptosis in cytokine primed eosinophils derived from hypereosinophilic patients and healthy donors on direct interaction with lung surfactant protein-D (SP-D) formulation.

Yet another object of the invention is the use of formulation with SP-D for the resolution of eosinophilic inflammations seen in eosinophil related diseases and disorders.

Still another object of the invention is to provide a pharmacologically active dose of SP-D in formulation, which lies in the range of 0.1-10 µg per ml for the induction of and/or increase in apoptosis in activated eosinophils.

SUMMARY OF THE INVENTION

The present invention provides the use of a formulation for inducing and/or increasing apoptosis in activated eosinophils comprising of complete or fragment(s) of native or recombinant human lung surfactant protein D. SP-D induces and increases apoptosis specifically in activated eosinophils derived from hypereosinophilic patients for the resolution of eosinophilia and eosinophil mediated pathogenic effects in eosinophil related diseases and disorders other than airway-hyperresponsiveness.

Accordingly the utility of the invention can be extended in human subjects in resolution of eosinophilia and eosinophil mediated pathogenic effects in eosinophil related diseases and disorders such as neuromuscular and respiratory diseases with eosinophilia, hypereosinophilic leukemias, hypereosinophilc syndromes (rare hematological diseases), skin diseases like eosinophilia-Myalgia syndrome, eosinophilic fascitis, eosinophilic cellulites, capillary leak syndromes (IL-2), Churg-Strauss syndrome, toxic oil syndrome, parasitosis, etc, where a large number of stimulated eosinophils accumulate and release a series of growth factors, cytokines, chemokines, bioactive lipid mediators, toxic oxygen metabolites and histotoxic cationic proteins. The present invention generally relates to a novel interaction of Surfactant protein-D with human eosinophils, wherein the molecule, induced and increased apoptosis of activated eosinophils derived from peripheral blood of individuals with hypereosinophilia. SP-D may thus play a significant role in maintenance of homoeostasis of eosinophils and tipping the balance of inflammation in favor of the beneficial vs. the damaging effects.

It is possible according to the invention to use SP-D for resolution of eosinophilic inflammations in eosinophil related diseases and disorders.

In an embodiment, the said formulation may comprise of lung surfactant protein-D.

In another embodiment, the said formulation may contain homologue(s), polypeptide(s), fragment(s), variant(s) or derivative(s) of SP-D.

In yet another embodiment the said pharmaceutical acceptable carriers in the formulation may be synthetic polymers, polylactic acid (PLA) and polylactic-co-glycolic acid (PLGA) sodium hyaluronate, calcium phosphate-polyethylene glycol (PEG) particles and oligosaccharide derivatives have been used to prepare protein/peptide microspheres for inhalation including both the oligosaccharide-lipid mix of Solidose and the lipid-based Pulmosphere In an embodiment to the invention, the lung surfactant protein used is recombinant or native SP-D.

In another embodiment to the invention the pharmacologically active dose of SP-D is in the range of 0.1-10 µg/ml.

In yet another embodiment to the invention, the pharmacologically active concentration of SP-D between 0.1 and 10 µg per ml of the protein causes 1.5-3 fold increase in activation state of eosinophils derived from patients in comparison with eosinophils from healthy donors.

In still another embodiment to the invention, the pharmacologically active concentration of SP-D at 10 µg per ml of the protein causes significantly increased apoptosis of eosinophils from patients (27.5% increase in apoptosis), while eosinophils from healthy donors showed a decreased apoptosis (13.2% decrease in apoptosis) in comparison to the respective experimental controls.

In still another embodiment to the invention, the pharmacologically active concentration of SP-D at 10 µg per ml of the protein causes increase in apoptosis in cytokine (IL-5) primed eosinophils (70.5%) from healthy donors to that of IL-5 primed eosinophils in absence of SP-D (53.2%).

BRIEF DESCRIPTION OF ACCOMPANYING FIGURES

FIG. 1 SP-D binding to human eosinophils: SP-D and recombinant human Surfactant protein-D (rhSP-D) showed dose dependent binding to human eosinophils derived from healthy donors. (B) rhSP-D showed a higher binding to eosinophils from healthy donors (each n=4). An unpaired Student's t test was used for statistical analysis. *p<0.05, rhSP-D binding to eosinophils from healthy donors versus hypereosinophilic patients. (C) Inhibition of SP-D binding to eosinophils by rhSP-D. A 48.26 fold molar excess of rhSP-D (224.5 µg/ml) could inhibit SP-D binding (10 µg/ml) to eosinophils by up to 50%.

Figure 2:
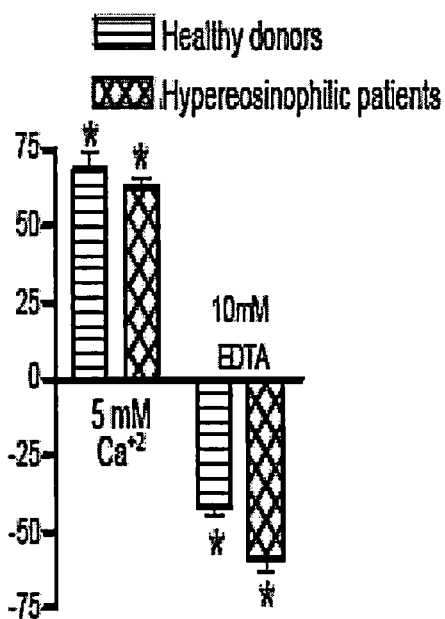

FIG. 2 Characterization of rhSP-D binding to eosinophils. In both the eosinophils derived from healthy donors and hypereosinophilic patients, rhSP-D binding increased in the presence of 5 mM calcium chloride, while presence of 10 mM EDTA inhibited rhSP-D binding to eosinophils. The data is expressed as percentage change in SP binding to eosinophils (increase or decrease in MFI) in comparison with their respective experimental control. Statistical significance of the percentage change with respect to control was evaluated by unpaired Student's t test. * p<0.05 versus respective experimental control.

Figure 3:
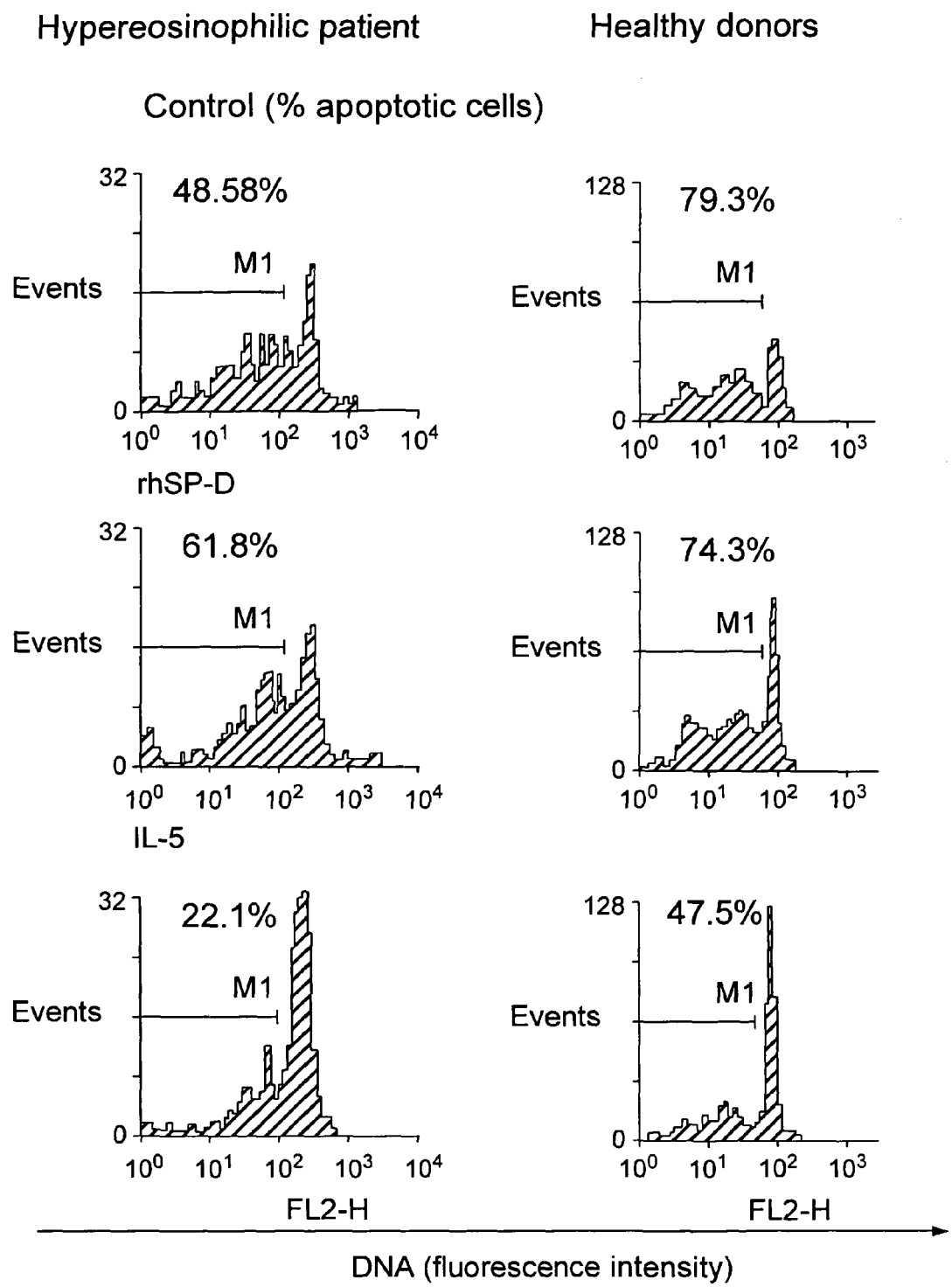

FIG. 3 Representative flowcytometry analysis for propidium iodide staining of DNA fragmentation in eosinophils, an indicator of apoptosis. Eosinophils from hypereosinophilic patients and healthy donors were incubated with rhSP-D (10 µg/ml) at 37° C. for 48 h. IL-5 (25 ng/ml) incubated cells with intact DNA were used to define marker (M1). Cells incubated with medium alone were taken as experimental control. X-axis is FL-2 region representing DNA content of the cells. The percentage apoptotic cells on the marker (M1) represent subdiploid DNA. The figure shows representative histograms from one of the independent experiments.

Figure 4:
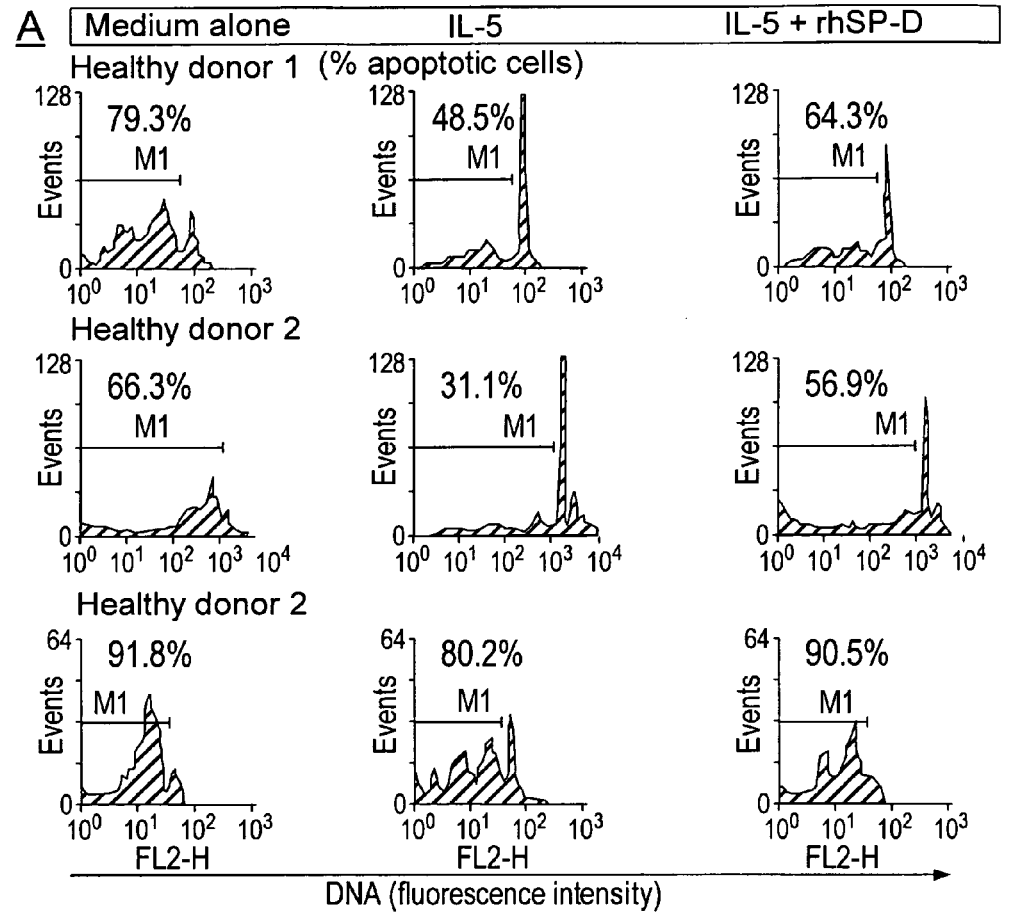
Figure 4:
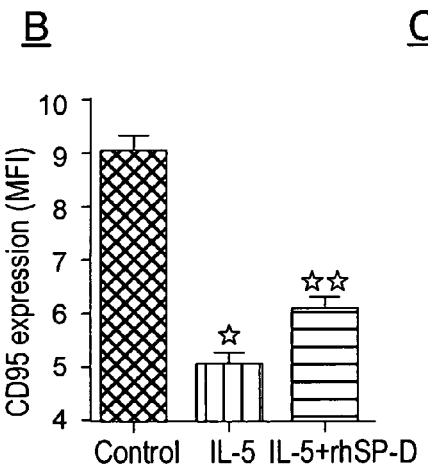
Figure 4:
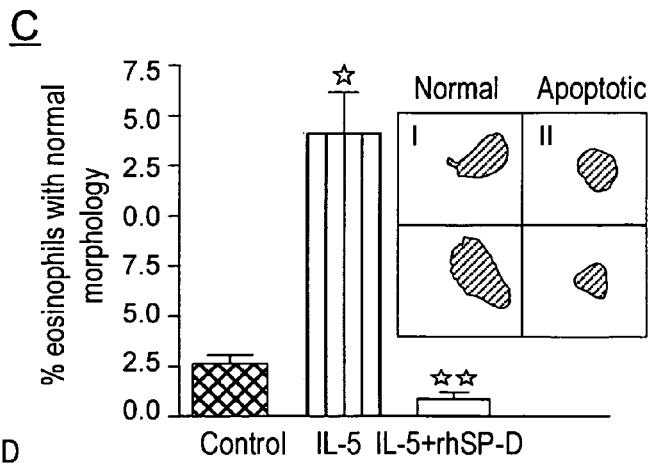

FIG. 4 Assessment of rhSP-D induced apoptosis in IL-5 incubated eosinophils from healthy donors. rhSP-D treated IL-5 primed eosinophils [IL-5+rhSP-D] of the healthy donors showed higher apoptosis in comparison to IL-5 primed eosinophils in absence of rhSP-D [IL-5] observed by [A] hypotonic propidium iodide staining, [B] increased CD95 expression and [C] Grünwald-Giemsa-staining by microscopic analysis. [A] Data shows representative histograms of the independent experiments from three healthy donors. Eosinophils incubated with IL-5 (25 ng/ml) [IL-5] having intact DNA, were used to define marker in all cases as described earlier. (B) The data shows MFI±SE of CD95 expression of representative one from three similar experiments and is compared by one-way ANOVA and Tukeys test. *p<0.05 versus [IL-5], **p<0.05 versus [Control] (cells cultured in medium alone). (C) Results are Mean±SE of percentage of viable cells for a characteristic experiment performed at least three times and compared by one-way ANOVA and Tukeys test. *p<0.05 versus [IL-5], **p<0.05 versus [Control] (cells cultured in medium alone). Inset: Eosinophils showing normal morphology, typical bilobed nucleus (Panel I), Apoptotic eosinophils, chromatin and cytoplasm condensation (Panel II).

DETAILED DESCRIPTION OF THE INVENTION

The present invention provides the use of a formulation for inducing and increasing apoptosis in activated eosinophils comprising of complete or fragment(s) of native or recombinant human lung surfactant protein D, the said use comprising steps of:

In an embodiment to the invention, isolation of human eosinophils was carried out from 50 ml peripheral blood of hypereosinophilic patients and healthy individuals by dextran sedimentation and density centrifugation, followed by negative immunomagnetic selection using antihuman CD16 microbeads. The standard protocol followed resulted in greater than 95% pure and 99% viable eosinophil population.

In an embodiment to the invention, native human SP-D was found to be free from IgG, IgM, and IgE contamination by ELISA using anti-human IgG, anti-human IgM, and anti-human IgE peroxidase conjugates, respectively.

In another embodiment to the invention, a recombinant homotrimer containing eight gly-x-y collagen repeat sequences, an alpha-helical, coiled-coil neck region, and the carbohydrate recognition domain of SP-D was expressed as inclusion bodies in *Escherichia coli*. This truncated SP-D, lacking the whole collagen domain and multimerising N-terminal region, retained the immunomodulatory properties displayed by full-length SP-D. Cross-linking studies indicated that rhSP-D exists predominantly as a trimer in solution. Its identity was confirmed by N-terminal sequencing, and was judged to be pure by SDS-PAGE and immunoblotting.

In another embodiment to the invention, native human surfactant protein-D (nhSP-D) and rhSP-D were labeled with FITC for the binding studies. The presence of unlabelled rhSP-D competitively inhibited the binding of nhSP-D-FITC to the human eosinophils.

In another embodiment to the invention, rhSP-D binding to human eosinophils was found to be calcium dependent and was inhibited in the presence of EDTA.

In another embodiment to the invention, the pharmacologically active concentration of nhSP-D and rhSP-D was used ranging between 0.1 and 10 µg per ml of the protein.

In another embodiment to the invention, there was an increase in apoptosis in eosinophils derived from hypereosinophilic patients in the presence of rhSP-D while eosinophils from healthy donors showed a decrease in apoptosis.

In another embodiment to the invention, there was an increase in apoptosis in cytokine (IL-5) primed eosinophils from healthy donors in the presence of rhSP-D to that of IL-5 primed eosinophils in absence of rhSP-D.

the Methodology Used for the Study is Given Below:
Hypereosiophilic Patients:

Five subjects (3 male and 2 female) with mean age 28 years, range 22-31, with elevated eosinophil counts and categorized as hypereosinophilic were included in this study. None of the subjects had received any medication for ≥24 h or steroids for ≥2 weeks before blood collection.

Healthy Donors:

The healthy donors (4 male and 2 female) (mean age 25 years, range 22-26) were defined on the basis of a lack of a clinical history of hypereosinophilia and had not been taking any medication 4 wk before the study.

Informed written consent was obtained from all the subjects. The project was approved by Institutional Human Ethical Committee and the guidelines were followed during sample collection.

Isolation of Human Eosinophils

Mixed granulocytes were obtained by dextran sedimentation and density centrifugation through Histopaque-1077 from the peripheral blood from hypereosinophilic patients and normals (anticoagulated with 0.4% (w/v) trisodium citrate (pH 7.4)) (25). Eosinophils were subsequently isolated from the granulocyte pellet by negative immunomagnetic selection (26) by Magnetic Cell Sorting of Human Leukocytes (MACS) kit using anti-human CD16 microbeads, VarioMACS magnetic cell separator and LD depletion columns (Miltenyi Biotec, CA, USA). The protocol for eosinophil separation was followed as described by the manufacturer. The CD16⁻ eosinophils were separated from the CD16⁺ microbeads tagged neutrophils by passing the cell suspension through the magnetic column. This resulted in greater than 95% pure eosinophil population. The eosinophil purity was assessed by Hinkleman's staining and May-Grunwald Giemsa staining. The viability of the purified eosinophils was determined by trypan blue dye exclusion and was consistently >99%. The eosinophils were washed and used further for the study.

Preparation of Native Human SP-D

Purified native human SP-D (obtained commercially) was judged to be pure by SDS-PAGE, western blot analysis, and amino acid composition. It was found to be free from IgG, IgM, and IgE contamination by ELISA using anti-human IgG, anti-human IgM, and anti-human IgE peroxidase conjugates, respectively.

Expression and Purification of Recombinant Human SP-D (rhSP-D)

A recombinant homotrimer containing eight gly-x-y collagen repeat sequences, an alpha-helical, coiled-coil neck region, and the carbohydrate recognition domain of rhSP-D was expressed as inclusion bodies in *Escherichia coli*. The inclusion bodies were isolated, denatured in 6 M urea and slowly renatured overnight in decreasing amounts of urea. The soluble rhSP-D was purified on a maltose-agarose column and contaminating LPS was removed using a polymixin-B column. Cross-linking studies indicated that rhSP-D exists predominantly as a trimer in solution (24). Its identity was confirmed by N-terminal sequencing, and was judged to be pure by SDS-PAGE and immunoblotting.

FITC Labeling of nhSP-D and rhSP-D

For FITC labeling, the surfactant protein was dialyzed against FITC labeling buffer (0.05 M boric acid, 0.2 M sodium chloride, pH 9.2) at 4° C. with 2-3 changes over 2 days. 20 µl of 5 mg per ml FITC in DMSO was then added for each mg of protein and incubated for 2 h at room temperature. The proteins were then dialyzed against buffer (0.1 M Tris-HCl, pH 7.4, 0.1% w/v sodium azide, 0.2 M NaCl) and stored at 4° C. The flurochrome to protein ratio of 5-6:1 was considered optimum for flow cytometric analysis (28).

rhSP-D and nhSP-D Binding to Human Eosinophils

To measure binding of FITC labeled rhSP-D or nhSP-D, purified eosinophils ($5\times10^5$ cells per ml) were washed and resuspended in the staining buffer (PBS with 0.1% sodium azide, 1.0% BSA) supplemented with 5 mM $CaCl_2$ and 1 mM $MgCl_2$ or as indicated. 100 µl of this suspension was co-incubated with FITC labeled rhSP-D at indicated concentrations for 45 minutes at 4° C. Cells were washed twice with washing buffer (PBS with 1% BSA) by centrifugation at 4° C. at 200×g and fixed with 4% formaldehyde in PBS.

For calcium-dependent studies, staining buffer containing 0, 0.1, 1 or 5 mM calcium chloride or buffer with 10 mM EDTA was used.

Flow cytometry was performed on at least 10,000 cells with a FACScan™ flow cytometer (Becton Dickinson). The specific mean fluorescence (SMF) was determined by subtracting the non-specific mean fluorescence (NMF) of the cells. The relative SMF (rSMF), which is the ratio of SMF emitted by bound surfactant protein to that of the NMF of the corresponding control, was calculated. The results were expressed as rSMF or % rSMF or as their Mean fluorescence Intensity (MFI) or % MFI.

Evaluation of Eosinophil Survival and Apoptosis

The effect of rhSP-D on the viability of eosinophils of hypereosinophilic patients and healthy donors was determined. For this, 100 µl of cells ($6\times10^5$ cells/ml) were suspended in medium (RPMI-1640 containing 10% FCS, 50 µM 2-mercaptoethanol, 1 mM sodium pyruvate and gentamicin (50 µg/ml)) and cultured with rhSP-D (0.1-10 µg/ml), IL-5 (25 ng/ml) or the culture medium alone and incubated for 48 h. The cells were then evaluated for any changes in viability or apoptotic cell numbers by hypotonic propidium iodide staining.

To study rhSP-D induced changes in the viability of in vitro primed cells, 100 µl of human eosinophils isolated from healthy donors ($6\times10^5$ cells/ml) were incubated with IL-5 (25 ng/ml) for 1 h [IL-5 primed eosinophils] and cultured with rhSP-D (0.1-10 µg/ml). The cells as such [control] or IL-5 alone (IL-5 primed eosinophils) [IL-5] or with rhSP-D (10 µg/ml) [IL-5+rhSP-D] were incubated for 48 and 60 h in the culture medium. The evaluation of apoptosis was done by hypotonic propidium iodide staining of DNA, CD95 expression (apoptotic cell marker) and Giemsa staining for analysis of cell morphology (29, 30).

Flowcytometric Analysis of DNA Content

Hypotonic propidium iodide (PI) solution was used to differentiate and identify the proportion of apoptotic eosinophils displaying a hypodiploid DNA peak to that of viable cells using modification of previous protocols (29). The method is demonstrated to be as sensitive as performing DNA agarose gel electrophoresis with the added advantage, that quantification of the degree of DNA fragmentation can be readily performed (29). For this, the washed eosinophils were gently resuspended in 200 µg of hypotonic propidium iodide (PI) solution (50 µg/ml in 0.1% sodium citrate plus 0.1% Triton X-100). The red PI fluorescence of the eosinophil nuclei was analyzed on at least 2,000 cells from each sample. For demarcating the two populations of normal and apoptotic eosinophils in each experiment, IL-5 incubated eosinophils were included, as IL-5 is known to maintain eosinophil survival and shows distinct peak for normal eosinophils. The number of cells belonging to the M region divided by the total cell count was expressed as the percentage cell apoptosis (% cell apoptosis).

CD95 Expression Analysis

Eosinophil expression of the apoptosis marker, CD95 or Fas-receptor (Apo-1) is demonstrated to increase as cells undergo apoptosis (30). The cell surface staining of CD95 on eosinophils was performed with the FITC labeled mouse anti-human CD95 IgG1 mAbs (Serotec Ltd., Oxford, UK). Incubation with the mAb was performed for 30 min at 4° C. The cells were then washed twice and analyzed by flow cytometry. The mouse IgG1 was used as an isotype control for the study.

Giemsa Staining

Apoptosis was confirmed by morphological analysis of cells spun onto cytospin slides, fixed with methanol and stained with May-Grünwald-Giemsa. The eosinophils were enumerated in randomly-selected fields and a minimum of 200 total cells were counted.

Advantages

The present invention is useful in providing the use of formulation with SP-D in resolution of eosinophilic inflammations by inducing and/or increasing apoptosis towards the beneficial effects in human subjects suffering eosinophil related diseases and disorders. These include neuromuscular and respiratory diseases with eosinophilia, hypereosinophilic leukemias, hypereosinophilc syndromes (rare hematological diseases), skin diseases like eosinophilia-Myalgia syndrome, eosinophilic fascitis, capillary leak syndromes (IL-2), Churg-Strauss syndrome, toxic oil syndrome, parasitosis, etc.

The invention is illustrated by the following examples which are given by way of illustration of the present invention and should not be construed to limit the scope of the present invention.

Example 1

Preparation of Eosinophils from Hypereosinophilic Patients and Healthy Donors

This example describes the preparation of human eosinophils from the peripheral blood. Mixed granulocytes were obtained by dextran sedimentation and density centrifugation through Histopaque-1077 from the human peripheral blood of hypereosinophilc patients and healthy donors (anticoagulated with 0.4% w/v trisodium citrate, pH 7.4) (25). Eosinophils were subsequently isolated from the granulocyte pellet by negative immunomagnetic selection by Magnetic Cell Sorting of Human Leukocytes (MACS) kit using anti-human CD16 microbeads, VarioMACS magnetic cell separator and LD depletion columns (Miltenyi Biotec, CA, USA) (26).

The $CD16^-$ eosinophils were separated from $CD16^+$ microbead tagged neutrophils by passing the cell suspension through the magnetic column that yielded >95% pure eosinophil population. The eosinophil purity was assessed by Hinkleman's staining and May-Grunwald Giemsa staining. The viability of purified eosinophils was determined by trypan blue dye exclusion and was consistently >99%.

Example 2

Preparation of Native and Recombinant Human Surfactant Protein-D

This example describes the preparation and purification of native human SP-D from the lung lavage obtained from alveolar proteinosis patients and preparation of a recombinant homotrimer containing eight gly-x-y collagen repeat sequences, an alpha-helical, coiled-coil neck region, and the carbohydrate recognition domain of rhSP-D, which is expressed under bacteriophage T7 promoter as inclusion bodies in *Escherichia coli* (24).

Example 3

Purification of Recombinant Human Surfactant Protein-D

This example describes the isolation of rhSP-D from the inclusion bodies, which is further denatured in 6 M urea and slowly renatured overnight by dialyzing against buffer containing decreasing amounts of urea. The soluble rhSP-D is purified on a maltose-agarose column and contaminating LPS removed using a polymyxin-B column.

The identity of the protein is confirmed by N-terminal sequencing and is judged to be pure by SDS-PAGE and immunoblotting.

Example 4

Estimating the Binding of Native and Recombinant Human SP-D to Human Eosinophils This example describes the binding of different concentrations of purified human rhSP-D (0.1-10 μg/ml) in phosphate buffered saline with 0.1% w/v sodium azide, 1% w/v BSA, 5 mM $CaCl_2$ and 1 mM $MgCl_2$, incubated with eosinophils prepared from peripheral blood of hypereosinophilic patients and healthy donors at $5\times10^5$ cells/ml counts. Prior to this the native and recombinant surfactant proteins are labeled with FITC as per standard methods. The eosinophils are incubated with FITC labeled surfactant proteins at various concentrations for 45 minutes at 4° C. The binding of rhSP-D to eosinophils derived from hypereosinophilic patients and healthy individuals was compared. The competitive experiment of native and recombinant surfactant protein was carried out. FITC-SP-D (10 μg/ml) was allowed to bind eosinophils in presence of unlabelled rhSP-D (10, 20, 50, 100 and 300 μg/ml) in the binding buffer. Flowcytometric analysis was performed on at least 10,000 cells using FACScan™ (Becton Dickinson) to check the binding of SP-D to human eosinophils. The specific mean fluorescence (SMF) is determined by subtracting the non-specific mean fluorescence (NMF) of the cells from the observed mean fluorescence intensity (MFI). The relative SMF (rSMF), which is the ratio of SMF emitted by bound surfactant protein to that of the NMF of the corresponding control, was calculated. The results expressed either as rSMF, or % rSMF or as their mean fluorescence intensity (MFI), or % MFI.

The binding of rhSP-D and nhSP-D to human eosinophils was dose dependent as shown in FIG. 1A. Native SP-D (10 μg/ml) showed a dose dependent binding to eosinophils that was inhibitable to 50% by unlabelled rhSP-D at 224.5 μg/ml concentration (FIG. 1C). Eosinophils from healthy donors showed a significantly higher binding to rhSP-D (10 μg/ml) as compared to eosinophils derived from hypereosinophilic patients (FIG. 1B).

Example 5

Estimating the Nature of Binding of Recombinant Human SP-D to Human Eosinophils

To evaluate the effect of calcium ion concentration on rhSP-D binding to human eosinophils, binding assays in the presence or absence of 5 mM calcium chloride or in the presence of 10 mM EDTA were carried out. The binding was estimated by flowcytometry as defined in the above example. rhSP-D (10 μg/ml) showed a significant increase in binding to eosinophils from hypereosinophilic patients and healthy donors in presence of 5 mM calcium and was inhibited in the presence of 10 mM EDTA (FIG. 2).

Example 6

Estimating Eosinophil Viability

The effect of rhSP-D on the viability of eosinophils of hypereosinophilic patients and healthy donors was determined. For this, 100 μl of cells ($6\times10^5$ cells/ml) were suspended in medium (RPMI-1640 containing 10% FCS, 50 μM 2-mercaptoethanol, 1 mM sodium pyruvate and gentamicin (50 μg/ml)) and cultured with rhSP-D (10 μg/ml), IL-5 (25 ng/ml) or the culture medium alone and incubated for 48 h. The cells were then evaluated for any changes in viability or apoptotic cell numbers by hypotonic propidium iodide staining. To study rhSP-D induced changes in the viability of in vitro primed cells, 100 μl of human eosinophils isolated from healthy donors ($6\times10^5$ cells/ml) were incubated with IL-5 (25 ng/ml) for 1 h [IL-5 primed eosinophils] and cultured with rhSP-D (10 μg/ml). The cells as such [control] or IL-5 alone (IL-5 primed eosinophils) [IL-5] or with rhSP-D (10 μg/ml) [IL-5+rhSP-D] were incubated for 48 and 60 h in the culture medium. The evaluation of apoptosis was done by hypotonic propidium iodide staining of DNA, CD95 expression (apoptotic cell marker) and Giemsa staining for analysis of cell morphology.

FIG. 3 depicts representative histogram of rhSP-D incubated eosinophils of a hypereosinophilic patient showing a significant increase in % apoptotic cells in comparison to the control (cells cultured in medium alone) and IL-5 cultured cells, measured by hypotonic PI staining of the cells. Eosinophils from hypereosinophilic patients showed an increase in the apoptosis in the presence of rhSP-D (% increase in apoptotic cell number relative to control, median, 27.5±5.33, n=4) while, eosinophils from healthy donors showed a decrease in apoptosis in presence of rhSP-D (% decrease in apoptotic cell number relative to control, median, 13.2±4.2, n=5) (48 h) (p=0.015, Mann Whitney test), suggesting significantly different responses from the two eosinophil types.

Incubation of rhSP-D (10 μg/ml) with IL-5 primed eosinophils from healthy donors resulted in a significant increase in apoptosis in these cells in comparison to the eosinophils incubated with IL-5 (25 ng/ml) alone observed at 48 h (data not shown) and maximally at 60 h (FIG. 4). rhSP-D treated IL-5 primed eosinophils [IL-5+rhSP-D] of the healthy donors showed higher apoptosis (% apoptotic cells, 70.57±10.19, n=3) in comparison to IL-5 primed eosinophils in absence of rhSP-D [IL-5] (% apoptotic cells, 53.2±13.68, n=3) observed by hypotonic propidium iodide staining (FIG. 4A). rhSP-D treated IL-5 primed eosinophils [IL-5+rhSP-D] (60 h) also showed a significant increase in CD95 expression in comparison to eosinophils incubated with IL-5 alone [IL-5] (FIG. 4B). FIG. 4C inset shows microscopic analysis of giemsa stained eosinophils. Eosinophils with a typical bilobed nucleus were considered as cells with normal morphology and were counted as viable (FIG. 4C inset I). Eosinophils with condensed nuclei were considered as cells with apoptotic morphology and were counted as apoptotic (FIG. 4C inset II). The microscopic analysis of rhSP-D (10 μg/ml) treated IL-5 primed eosinophils [IL-5+rhSP-D] showed a significant decrease in cells with normal morphology in comparison to IL-5 primed eosinophils (FIG. 4C).

1. Rothenberg, M. E. 1998. Eosinophilia. *The New England Journal of Medicine.* 338(22): 1592-1600.
2. Posada de la Paz M, Philen R M, Borda A I. 2001. Toxic oil syndrome: the perspective after 20 years. Epidemiol Rev. 23(2):231-47. Review.
3. Crouch E C. 2000. Surfactant protein-D and pulmonary host defense. Respir Res. 1(2):93-108. Review.
4. Whitsett J A. 2005. Surfactant proteins in innate host defense of the lung. Biol Neonate. 88(3):175-80. Review.
5. Madan, T., Kaur, S., Saxena, S., Singh, M., Kishore, U., Thiel, S., Reid, K. B. & Sarma, P. U. (2005a). Role of collectins in innate immunity against aspergillosis. *Med Mycol* 43 Suppl 1, S155-63.
6. Madan, T., et al. 1997. Lung surfactant proteins A and D can inhibit specific IgE binding to the allergens of *Aspergillus fumigatus* and block allergen-induced histamine release from human basophils. Clin. Exp. Immunol. 110:241-249.
7. Wang, J. Y., Shieh, C. C., You, P. F., Lei, H. Y., and Reid, K. B. M. 1998. Inhibitory effect of pulmonary surfactant proteins A and D on allergen induced lymphocyte proliferation and histamine release in children with asthma. Am. J. Respir. Crit. Care Med. 158:510-518.
8. Borron, P. J., et al. 1998. Recombinant rat surfactant-associated protein D inhibits human T lymphocyte proliferation and IL-2 production. J. Immunol. 161:4599-4603.
9. Kishore, U., Madan, T., Sarma, P. U., Singh, M., Urban, B. C. & Reid, K. B. (2002). Protective roles of pulmonary surfactant proteins, SP-A and SP-D, against lung allergy and infection caused by *Aspergillus fumigatus. Immunobiology* 205, 610-8.
10. Singh, M., T. Madan, P. Waters, S. K. Parida, P. U. Sarma, and U. Kishore. 2003. Protective effects of a recombinant fragment of human surfactant protein D in a murine model of pulmonary hypersensitivity induced by dust mite allergens. Immunol. Lett. 86: 299-307.
11. Erpenbeck V J, Ziegert M, Cavalet-Blanco D, Martin C, Baelder R, Glaab T, Braun A, Steinhilber W, Luettig B, Uhlig S, Hoymann H G, Krug N, Hohlfeld J M. 2006. Surfactant protein D inhibits early airway response in *Aspergillus fumigatus*-sensitized mice. Clin Exp Allergy. 36(7):930-40.
12. Palaniyar, N., Clark, H., Nadesalingam, J., Hawgood, S., and Reid, K. B. 2003. Surfactant protein D binds genomic DNA and apoptotic cells, and enhances their clearance, in vivo. Ann. N. Y. Acad. Sci. 1010: 471.
13. Mahajan et al, Journal of Allergy and Clinical Immunology, Volume 117, Issue 2, Supplement 1, February 2006, Page S64 (abstract presented in AAAAI meeting 2006).
14. von Bredow C., Hartl, D., Schmid, K., Schabaz, F., Brack, E., Reinhardt, D. and Griese, M. 2006. Surfactant protein D regulates chemotaxis and degranulation of human eosinophils. Clin Exp Allergy. 36(12):1566.
15. Whitsett; Jeffrey A. 2000. Surfactant protein D for the prevention and diagnosis of pulmonary emphysema. U.S. Pat. No. 6,838,428
16. Clark Howard. 2004. Recombinant surfactant protein D compositions and methods of use thereof. United States Patent 20040259201.
17. IKEGAMI, Machiko; WHITSETT, Jeffrey, A. 2007. Surfactant protein-D for prevention and treatment of lung infections and sepsis. Patent WO2007056195.
18. Madan, T., Kishore, U., Singh, M., Strong, P., Clark, H., Hussain, E. M., Reid, K. B. and Sarma, P. U. 2001. Surfactant proteins A and D protect mice against pulmonary hypersensitivity induced by *Aspergillus fumigatus* antigens and allergens. *J. Clin. Invest.* 107: 467.
19. Kishore U, Greenhough T J, Waters P, Shrive A K, Ghai R, Kamran M F, Bernal A L, Reid K B, Madan T, Chakraborty T. Surfactant proteins SP-A and SP-D: structure, function and receptors. Mol Immunol. 2006 March; 43(9): 1293-315.
20. Haczku A, Vass G, Kierstein S. 2004. Surfactant protein D and asthma. *Clin Exp Allergy.* 34(12):1815-8. Review.
21. Pellissier J F, Figarella-Branger D, Serratrice G. 1998. Neuromuscular diseases with eosinophilia. Med Trop (Mars). 58(4 Suppl):471-6. Review.
22. Bunc M, Remskar Z, Brucan A. 2001. The idiopathic hypereosinophilic syndrome. 2001. *Eur J Emerg Med.* 8(4):325-30.
23. Kamb M L, Murphy J J, Jones J L, Caston J C, Nederlof K, Horney L F, Swygert L A, Falk H, Kilbourne E M. 1992. Eosinophilia-myalgia syndrome in L-tryptophan-exposed patients. JAMA. 267(1):77-82.
24. Kishore, U., Wang, J. Y., Hoppe, H. J. & Reid, K. B. 1996. The alpha-helical neck region of human lung surfactant protein D is essential for the binding of the carbohydrate recognition domains to lipopolysaccharides and phospholipids. *Biochem J* 318 (Pt 2), 505-11.
25. Koenderman, L., Kok, P. T., Hamelink, M. L., Verhoeven, A. J. & Bruijnzeel, P. L. 1988. An improved method for the isolation of eosinophilic granulocytes from peripheral blood of normal individuals. *J Leukoc Biol* 44, 79-86.
26. Hansel, T. T., De Vries, I. J., Iff, T., Rihs, S., Wandzilak, M., Betz, S., Blaser, K. & Walker, C. 1991. An improved immunomagnetic procedure for the isolation of highly purified human blood eosinophils. *J Immunol Methods* 145, 105-10.
27. Strong, P., Kishore, U., Morgan, C., Lopez Bernal, A., Singh, M. & Reid, K. B. (1998). A novel method of purifying lung surfactant proteins A and D from the lung lavage of alveolar proteinosis patients and from pooled amniotic fluid. *J Immunol Methods* 220, 139-49.
28. Holmes K., Fowlkes B. J. (1996). Immunofluorescence and Cell Sorting. *Current Protocols in Immunology,* 2nd ed J. E. Coligan, A. M. Kruisbeek, D. H. Margulies, E. M. Shevach and W. Strober, eds. John Wiley and Sons, Inc. 5.3.1-5.3.13.
29. Nicoletti, I., Migliorati, G., Pagliacci, M. C., Grignani, F. & Riccardi, C. (1991). A rapid and simple method for measuring thymocyte apoptosis by propidium iodide staining and flow cytometry. *J Immunol Methods* 139, 271-9.
30. Hebestreit, H., Yousefi, S., Balatti, I., Weber, M., Crameri, R., Simon, D., Hartung, K., Schapowal, A., Blaser, K. & Simon, H. U. (1996). Expression and function of the Fas receptor on human blood and tissue eosinophils. *Eur J Immunol* 26, 1775-80.

The invention claimed is:

1. A method for treating an eosinophil mediated disorder comprising administering a formulation comprising human Surfactant Protein-D (SP-D) to a subject in need thereof, wherein the eosinophil mediated disorder is eosinophilic cardiomyopathy, eosinophilic gastroenteritis, graft versus host disease, drug reaction, eosinophilic pneumonia, episodic angioedema with eosinophilia, inflammatory bowel disease, eosinophilic leukemia, food enteropathy, neuromuscular disease with eosinophilia, eosinophilia-Myalgia syndrome, eosinophilic fascitis, capillary leak syndrome, Churg-Strauss syndrome, toxic oil syndrome, chronic sinusitis, cirrhosis or two or more thereof.

2. The method as claimed in claim 1, wherein the human Surfactant Protein D (SP-D) used is recombinant human SP-D or native hSP-D.

3. The method as claimed in claim 1, wherein the formulation of SP-D administered is in a concentration range of 0.1 to 10 µg of SP-D/ml.

4. The method as claimed in claim 1, wherein the formulation comprises a pharmaceutical acceptable carrier.

5. The method as claimed in claim 4, wherein the pharmaceutical carrier is selected from the group consisting of synthetic polymers, polylactic acid (PLA), polylactic-co-glycolic acid (PLGA), sodium hyaluronate, calcium phosphate-polyethylene glycol (PEG) particles and oligosaccharide derivatives.

6. The method according to claim 1, wherein the eosinophil mediated disorder is neuromuscular disease with eosinophilia, eosinophilic leukemia, eosinophilia-Myalgia syndrome, eosinophilic fascitis, capillary leak syndrome, Churg-Strauss syndrome, toxic oil syndrome or chronic sinusitis.

7. The method as claimed in claim 1, wherein the eosinophils are human eosinophils.

* * * * *